United States Patent [19]
Pfirmann et al.

[11] Patent Number: 5,965,775
[45] Date of Patent: Oct. 12, 1999

[54] PROCESS FOR THE PREPARATION OF 3,5-DIFLUOROANILINE

[75] Inventors: Ralf Pfirmann, Griesheim; Stefan Krause, Frankfurt, both of Germany

[73] Assignee: Clariant GmbH, Frankfurt, Germany

[21] Appl. No.: 09/078,012

[22] Filed: May 13, 1998

[30] Foreign Application Priority Data

May 15, 1997 [DE] Germany ............................ 197 20 341

[51] Int. Cl.$^6$ .................................................. C07C 209/36
[52] U.S. Cl. ............................................. 564/407; 564/405
[58] Field of Search ...................................... 564/407, 405

[56] References Cited

U.S. PATENT DOCUMENTS

| | | | |
|---|---|---|---|
| 4,508,922 | 4/1985 | Ratton ...................................... | 564/407 |
| 4,521,622 | 6/1985 | Andoh et al. ........................... | 564/406 |
| 5,294,742 | 3/1994 | Schach et al. . | |
| 5,510,533 | 4/1996 | Kobayashi et al. ..................... | 564/507 |
| 5,723,669 | 3/1998 | Goodbrand et al. .................... | 564/307 |

FOREIGN PATENT DOCUMENTS

| | | |
|---|---|---|
| 460639 | 12/1991 | European Pat. Off. . |
| 562435 | 9/1993 | European Pat. Off. . |
| WO 9602493 | 2/1996 | WIPO . |
| WO 98/05610 | 2/1998 | WIPO . |

OTHER PUBLICATIONS

CA116:105818, 1991.
J. Amer. Chem. Soc. 81, 94–101 (1959).
Shirley, Dickerson and Finger, J. Fluorine Chem., 2 (1972/73) pp. 19–26.
R. Schwesinger et al., Angew. Chem. 103 (1991) pp. 1376.
R. Schwesinger et al., Chem. Ber. 127 (1994) pp. 2435–2454.

*Primary Examiner*—Brian M. Burn
*Attorney, Agent, or Firm*—Scott E. Hanf

[57] ABSTRACT

The present invention relates to a process for the preparation of 3,5-difluoroaniline by reacting 3,5-difluorochlorobenzene with ammonia in the presence of a solvent in the presence of a copper compound and at least one metal selected from the group consisting of copper, iron, cobalt, nickel, chromium, molybdenum and zinc, at 100 to 250° C.

22 Claims, No Drawings

PROCESS FOR THE PREPARATION OF 3,5-DIFLUOROANILINE

The present invention relates to an advantageous process for the preparation of 3,5-difluoroaniline.

3,5-Difluoroaniline is an important compound, inter alia for the preparation of industrial chemicals.

On account of the importance of 3,5-difluoroaniline as a synthetic building block—as is clear, for example, from J. Amer. Chem. Soc. 81, 94–101 (1959)—there has been no lack of attempts to develop syntheses for the preparation of 3,5-difluoroaniline.

Thus WO 96/02493, starting from 2,4-difluoroaniline, discloses a synthesis proceeding via five stages. 2,4-Difluoroaniline is first reacted with acetic anhydride, the resulting acetanilide is nitrated by means of $HNO_3/H_2SO_4$, the acetyl radical is removed and 2,4-difluoro-6-nitroaniline is obtained. By reaction of the 2,4-difluoro-6-nitroaniline with sodium nitrite, the amino group can be removed and 3,5-difluoronitrobenzene is obtained, which can be converted into 3,5-difluoroaniline by reduction.

A synthesis proceeding via four stages can be taken from EP 562 435. 2,4,5-Trichloronitrobenzene is first reacted with an alkali metal fluoride to give 5-chloro-2,4-difluoronitrobenzene. By means of chlorinating denitration the 5-chloro-2,4-difluoronitrobenzene can be converted to 1,3-dichloro-4,6-difluorobenzene. The 1,3-dichloro-4,6-difluorobenzene is nitrated to give 2,6-dichloro-3,5-difluoronitrobenzene. The desired 3,5-difluoroaniline can be prepared from the 2,6-dichloro-3,5-difluoronitrobenzene by reaction with hydrogen with elimination of hydrogen chloride and reduction of the nitro group.

EP 460 639 describes a three-stage preparation of 3,5-difluoroaniline. Starting from 5-chloro-2,4,6-trifluoroisophthalic acid, this is decarboxylated to give 2-chloro-1,3,5-trifluorobenzene. By reaction of the 2-chloro-1,3,5-trifluorobenzene with copper and water at 300° C., 1,3,5-trifluorobenzene can be prepared. According to Example 6 of EP 460 639, 1,3,5-tri-fluorobenzene is reacted with methanol saturated with ammonia at 200° C. for 60 hours and 3,5-difluoroaniline is obtained.

The preparation processes described above proceed via several stages and necessitate a correspondingly high outlay. The starting substances needed for these processes—2,4-difluoroaniline, 2,4,5-trichloro-nitrobenzene and 5-chloro-2,4,6-trifluoroisophthalic acid—are compounds which are not easily accessible, but are mostly obtainable with the aid of syntheses proceeding via several stages. As a result, the working outlay for the preparation of 3,5-difluoroaniline is additionally increased.

In view of this, there is an interest in making available a process for the preparation of 3,5-difluoroaniline which does not have these disadvantages. It should open up a simple, short synthetic route, be able to be carried out with a justifiable working outlay and yield the desired 3,5-difluoroaniline in acceptable yields.

This object is achieved by a process for the preparation of 3,5-difluoro-aniline. It comprises reacting 3,5-difluorochlorobenzene with ammonia in the presence of a solvent in the presence of a copper compound and at least one metal selected from the group consisting of copper, iron, cobalt, nickel, chromium, molybdenum and zinc, at 100 to 250° C.

The 3,5-difluorochlorobenzene needed for the process according to the invention can be prepared by reaction of 1,3,5-trichlorobenzene with an alkali metal fluoride in the presence of a solvent or of a suitable catalyst.

The reaction of 1,3,5-trichlorobenzene with KF or a KF/CsF mixture in dimethyl sulfoxide leads to 3,5-difluorochlorobenzene. This type of reaction, however, necessitates very high temperatures, namely 280 or 275° C., and yields the 3,5-difluorochlorobenzene in 47.7% or 40.5% yield (compare also Shiley, Dickerson and Finger, J. Fluorine Chem., 2 (1972/73), pages 19 to 26). High reaction temperatures of this type, however, are very demanding on the wear resistance of the reactor containers and stirrers used and can favor the formation of by-products.

A particularly favorable variant of this reaction is described in the non prior-published German Patent Application (reference 196 31 854.8). This application relates to a process for the preparation of fluorine-containing compounds by reacting a compound, which contains halogen which can be replaced by fluorine, with a fluoride or a mixture of fluorides of the formula $$MeF \qquad (I),$$

in which Me is an alkaline earth metal ion, $NH_4^+$ ion or alkali metal ion, in the presence of a compound or of a mixture of compounds of the formula

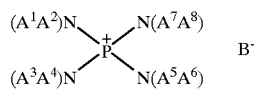

(II)

in which $A^1, A^2, A^3, A^4, A^5, A^6, A^7, A^8$ independently of one another are identical or different and are a straight-chain or branched alkyl or alkenyl having 1 to 12 carbon atoms, cycloalkyl having 4 to 8 carbon atoms, an aryl having 6 to 12 carbon atoms, an aralkyl having 7 to 12 carbon atoms, or $A^1 A^2, A^3 A^4, A^5 A^6, A^7 A^8$ independently of one another are identical or different and are bonded to one another directly or via O or N-$A^9$ to give a ring having 3 to 7 ring members, $A^9$ is an alkyl having 1 to 4 carbon atoms and $B^-$ is a monobasic acid radical or the equivalent of a polybasic acid radical, at a temperature from 40 to 260° C. in the presence or absence of a solvent.

The abovementioned compound of the formula (II) or the mixture of compounds of this type proves to be a suitable catalyst for the reaction, for example, of 1,3,5-trichlorobenzene by means of alkali metal fluorides to give 3,5-difluorochlorobenzene.

The fluoride of the formula (I) employed is calcium fluoride, ammonium fluoride, lithium fluoride, sodium fluoride, potassium fluoride, rubidium fluoride, cesium fluoride or a mixture thereof, in particular lithium fluoride, sodium fluoride, potassium fluoride, rubidium fluoride, cesium fluoride or a mixture thereof, preferably sodium fluoride, potassium fluoride, cesium fluoride or a mixture thereof, particularly preferably potassium fluoride, cesium fluoride or a mixture thereof. It is often sufficient to employ potassium fluoride on its own.

The compounds of the formula (II) can be prepared, for example, by reaction of phosphorus pentachloride with dialkylamines. The reaction using dimethylamine can be seen from the following equation.

It is also possible, however, to react phosphorus pentachloride in stages with different secondary amines, for example dialkylamines, in order to obtain unsymmetrically substituted compounds of the formula (II). Other possibilities of synthesizing compounds of the formula (II) are described by R. Schwesinger et al., Angew. Chem. 103 (1991) 1376 and R. Schwesinger et al., Chem. Ber. 127 (1994) 2435 to 2454.

Customarily, a compound of the formula (II) is employed in which $B^-$ is $F^-$, $Cl^-$, $Br^-$, $I^-$, $HF_2^-$, $BF_4^-$, $C_6H_5SO_3^-$, p-$CH_3$-$C_6H_5SO_3^-$, $HSO_4^-$, $PF_6^-$, $CF_3SO_3^-$, in particular $F^-$, $Cl^-$, $Br^-$, $I^-$, $HF_2^-$, $BF_4^-$.

The compound of the formula (II) is employed in an amount from 0.5 to 35, in particular 1 to 30, preferably 3 to 25, % by weight, based on the compound which contains halogen replaceable by fluorine.

In order not to be exclusively dependent on the above details in % by weight, it is possible in a large number of cases to employ the compound of the formula (II) in an amount from 0.1 to 3, in particular from 0.4 to 5, preferably 0.5 to 1, mol %, based on the compound which contains halogen replaceable by fluorine. These amounts customarily prove to be adequate.

Without claiming to be complete, the following may be mentioned as examples of compounds of the formula (II).
Tetrakis(dimethylamino)phosphonium chloride
Tetrakis(diethylamino)phosphonium chloride
Tetrakis(dimethylamino)phosphonium bromide
Tetrakis(diethylamino)phosphonium bromide
Tetrakis(dipropylamino)phosphonium chloride or bromide
Tris(diethylamino)(dimethylamino)phosphonium chloride or bromide
Tetrakis(dibutylamino)phosphonium chloride or bromide
Tris(dimethylamino)(diethylamino)phosphonium chloride or bromide
Tris(dimethylamino)(cyclopentylamino)phosphonium chloride or bromide
Tris(dimethylamino)(dipropylamino)phosphonium chloride or bromide
Tris(dimethylamino)(dibutylamino)phosphonium chloride or bromide
Tris(dimethylamino)(cyclohexylamino)phosphonium chloride or bromide
Tris(dimethylamino)(diallylamino)phosphonium chloride or bromide
Tris(dimethylamino)(dihexylamino)phosphonium chloride or bromide
Tris(diethylamino)(dihexylamino)phosphonium chloride or bromide
Tris(dimethylamino)(diheptylamino)phosphonium chloride or bromide
Tris(diethylamino)(diheptylamino)phosphonium chloride or bromide
Tetrakis(pyrrolidino)phosphonium chloride or bromide
Tetrakis(piperidino)phosphonium chloride or bromide
Tetrakis(morpholino)phosphonium chloride or bromide
Tris(piperidino)(diallylamino)phosphonium chloride or bromide
Tris(pyrrolidino)(ethylmethylamino)phosphonium chloride or bromide
Tris(pyrrolidino)(diethylamino)phosphonium chloride or bromide.

It is possible to use as a catalyst a compound of the formula (II) or a mixture of two or more compounds of the formula (II). This turns out to be particularly simple if mixtures of compounds of the formula (II), such as are obtained in the synthesis, are used.

The process can be carried out as previously already mentioned, in the presence or absence of a solvent. If solvents are used, then both dipolar aprotic solvents and aprotic solvents as well as protic solvents are suitable. Suitable dipolar aprotic solvents are, for example, dimethyl sulfoxide (DMSO), dimethyl sulfone, sulfolane (TMS), dimethylformamide (DMF), dimethylacetamide, 1,3-dimethylimidazolin-2-one, N-methylpyrrolidone, hexamethylphosphoramide, acetonitrile and benzonitrile. These solvents can also be used as a mixture.

Suitable aprotic solvents without marked dipolar character are aromatic hydrocarbons or chlorinated aromatic hydrocarbons, for example, benzene, toluene, ortho-, meta- or para-xylene, technical mixtures of isomeric xylenes, ethylbenzene, mesitylene, ortho-, meta- or para-chlorotoluene, chlorobenzene and ortho-, meta- or para-dichlorobenzene. Mixtures of these solvents can also be used.

The aprotic or dipolar aprotic solvent can be used in any desired amount, for example 5 to 500% by weight, preferably, however, small amounts in the range from 5 to 30% by weight, based on the compound which contains halogen replaceable by fluorine. When using protic solvents, the amounts employed lie in the range from 0.1 to 5, preferably 0.1 to 2, % by weight, based on the compound which contains halogen replaceable by fluorine.

The reaction temperature depends on the nature of the compound which contains halogen replaceable by fluorine. Thus compounds which are comparatively slow to react as a rule necessitate higher reaction temperatures, while comparatively reactive starting substances can be reacted successfully even at relatively low temperatures.

The reaction of 1,3,5-trichlorobenzene can be carried out highly successfully even at temperatures of, for example, 170 to 210° C. Also compare the example in the Experimental Section.

With the aid of the abovementioned catalysts (compounds of the formula (II)), it is thus possible to react the 1,3,5-trichlorobenzene, which is comparatively very slow to react, with an alkali metal fluoride to give the desired 3,5-difluorochlorobenzene. The preceding details with respect to the reaction of 1,3,5-trichlorobenzene serve to illustrate the process of the non prior-published German Application (reference 196 31 854.8) in greater detail.

By means of the process according to the invention, a short direct synthesis route is now opened up which, starting from 1,3,5-trichloro-benzene, leads in only two steps to the desired 3,5-difluoroaniline. 3,5-Difluorochlorobenzene is first prepared from 1,3,5-trichlorobenzene and the 3,5-difluorochlorobenzene is then reacted according to the present invention to give 3,5-difluoroaniline. This synthesis route is short and, since it starts from 1,3,5-trichlorobenzene, which is available in industrial amounts, is of particular interest.

The reaction proceeds according to the following reaction scheme:

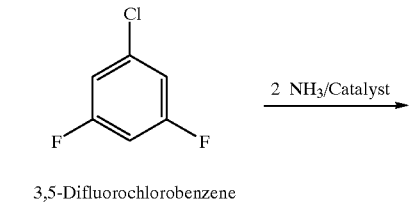

3,5-Difluorochlorobenzene

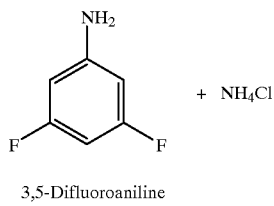

3,5-Difluoroaniline

By means of the process according to the invention it is surprisingly possible to replace the chlorine substituents of the 3,5-difluorochloro-benzene with high selectivity by an amino group. This was not to be expected, since the 3,5-difluorochlorobenzene contains not less than three halogen substituents, namely two fluorine radicals and a chlorine radical, which each can be replaced by an amino group. On the contrary, it had to be expected that products would also be formed in which a fluorine substituent or two halogen substituents, for example the chlorine radical and a fluorine radical, have each been replaced by an amino group.

It was not to be expected that with the aid of the process according to the invention it would be possible to replace the chlorine substituents in 3,5-difluorochlorobenzene exclusively with high selectivity by an amino group.

It is possible to react ammonia and 3,5-difluorochlorobenzene in a stoichiometric ratio or with a very large excess of ammonia. Customarily, ammonia and 3,5-difluorochlorobenzene are employed in the molar ratio (1 to 200):1, in particular (1:100):1.

In a large number of cases, it has proven favorable to employ ammonia and 3,5-difluorochlorobenzene in the molar ratio (5 to 30):1, in particular (10 to 20):1.

It is possible to employ ammonia in gaseous or liquid form or dissolved in a solvent.

The reaction is carried out in the presence of a solvent. Solvents employed are water or a mixture containing water and a water-soluble solvent, in particular water.

Suitable water-soluble solvents are protic solvents such as alcohols, in particular aliphatic alcohols having 1 to 4 carbon atoms, and/or aprotic solvents such as tetrahydrofuran, dioxane, sulfolane, N-methyl-pyrrolidone, dimethylacetamide, dimethylformamide, diethylacetamide, diethylformamide or N,N,N,N-tetramethylurea.

If a mixture containing water and a water-soluble solvent is used, then this mixture should contain at least 60, in particular at least 80, % by weight of water, customarily 60 to 99, in particular 75 to 98, % by weight of water. It is thereby ensured that ammonia is dissolved in a sufficient extent in order to be able to complete the reaction successfully.

It is particularly simple to use ammonia in the form of an aqueous solution.

Ammonia is employed in the form of an aqueous solution containing 10 to 35, in particular 15 to 30, % by weight of ammonia.

The catalyst system necessary for the reaction consists of a copper compound and at least one metal, in particular of a copper compound and a metal selected from the group consisting of copper, iron, cobalt, nickel, chromium, molybdenum and/or zinc.

The copper compound employed is a copper(I) compound, a copper(II) compound or a mixture thereof, in particular a copper(I) compound or a mixture thereof.

The copper compound employed is a copper(I) salt or copper(I) oxide, in particular copper(I) chloride, copper(I) bromide or copper(I) iodide, preferably copper(I) chloride or copper(I) iodide. Copper(I) chloride is particularly suitable.

The reaction is carried out in the presence of at least one metal selected from the group consisting of copper, iron, cobalt and nickel, in particular selected from the group consisting of copper, iron and cobalt.

The metal employed can preferably be copper or iron. It has proven to be particularly favorable to employ copper as a metal in a number of cases.

It may be expressly mentioned here that the catalyst system contains a metal of the abovementioned group in addition to the copper compound. Only this combination of copper compound and metal has proven to be a selectively acting catalyst system which makes the desired 3,5-difluoroaniline accessible in good yields.

Customarily, the copper compound and 3,5-difluorochlorobenzene are employed in the molar ratio (0.05 to 1.5):1, in particular (0.1 to 0.6):1, preferably (0.15 to 0.4):1.

As a rule, (0.05 to 1.5), in particular (0.1 to 0.6), preferably (0.15 to 0.4) g atom of metal are employed per mole of 3,5-difluorochlorobenzene.

It has often proven adequate to carry out the reaction at 130 to 200° C., in particular 140 to 190° C.

The process can be carried out continuously or batchwise. It can be carried out under normal pressure or elevated pressure. It is particularly simple to complete the process under the autogenous pressure in each case arising under the reaction conditions used. In this case, pressures from 5 to 100 bar, in particular 10 to 60 bar, are customary.

The starting material used is advantageously a 3,5-difluorochlorobenzene prepared from 1,3,5-trichlorobenzene by fluorine-chlorine exchange, for example a 3,5-difluorochlorobenzene prepared according to the abovementioned German Application (reference 196 31 854.8).

The following examples describe the invention in greater detail without restricting it.

EXPERIMENTAL SECTION

Preparation of 3,5-difluorochlorobenzene (Example 12 of the non prior-published German Application (reference 196 31 854.8))

Preparation of 1-fluoro-3,5-dichlorobenzene and 1, 3-difluoro-5-chloro-benzene (3,5-difluorochlorobenzene) by reaction of 1,3,5-trichlorobenzene by means of tetrakis(diethylamino) phosphonium bromide A 500 ml four-necked flask which is equipped with a thermometer, anchor stirrer and reflux condenser with a bubble counter is charged with 181.5 g (1 mol) of 1,3,5-trichlorobenzene, 136.8 g (2.4 mol) of potassium fluoride and 7.98 g (0.02 mol) of tetrakis(diethylamino) phosphonium bromide. The mixture is then heated with stirring to the prespecified reaction temperature of 180° C. and allowed to react for 10 hours. After completion of the reaction, the reaction mixture is allowed to cool and is dissolved in methylene chloride, insoluble constituents (salts such as KCl, KF) are filtered off and the valuable products (1-fluoro-3,5-dichlorobenzene and 1,3-difluoro-5-chlorobenzene (3,5-difluorochlorobenzene)) are purified by fractional distillation.

The conversion is 100%. 1-Fluoro-3,5-dichlorobenzene: 50% yield; 1,3-difluoro-5-chlorobenzene (3,5-difluorochlorobenzene): 37% yield.

Examples 1 to 6

Preparation of 3,5-difluoroaniline by reaction of 3, 5-difluorochlorobenzene in the presence of a copper compound and of a metal A 100 ml autoclave having a Teflon liner is charged with the amounts of 3,5-difluorochlorobenzene, copper compound (Examples 1 to 3: CuCl); Examples 4 and 6: CuI; Example 5: Cu$_2$O), metal (Examples 1 to 5: copper powder; Example 6: steel turnings) and aqueous ammonia solution (25% by weight ammonia) indicated in the following table. The autoclave is closed and the reaction is carried out with stirring at the temperature and for the time indicated in the table. The contents of the autoclave are cooled and filtered through a glass frit. The filtrate is extracted with approximately 150 ml of methylene chloride. The content of 3,5-difluoroaniline and 3,5-difluorochlorobenzene shown in the table is then determined by gas chromatography with an internal standard.

If the valuable product (3,5-difluoroaniline) is to be isolated, the methylene chloride extract is distilled. In this case, methylene chloride passes over first at normal pressure as a forerun, then at approximately 116° C. and normal pressure any 3,5-difluorochlorobenzene distils off and then, at approximately 150° C. and 20 mbar, 3,5-difluoroaniline.

is carried out as described in Examples 1 to 6. The addition of a copper compound is dispensed with.

In addition to decomposition products (approximately 19%), considerable amounts of fluoroaniline (approximately 20%) and 3-fluoro-5-chloroaniline (approximately 30%) are formed. The abovementioned percentage details in brackets refer to estimation of uncalibrated GC analysis data. The conversion is 90% of theory; the content of 3,5-difluoroaniline is only 21% of theory.

The reaction conditions (amounts used, temperatures, times) and analysis data (content of 3,5-difluoroaniline and 3,5-difluorochlorobenzene based on GC analysis with an internal standard) used in Examples 1 to 6 and in the Comparison Examples A and B are compiled in the following table.

TABLE

| | Amounts used | | | | Reaction conditions | | Content of reaction product according to GC* | |
|---|---|---|---|---|---|---|---|---|
| Examples | 3,5-Difluoro-chloro-benzene | Copper compound | Metal | Ammonia as a 25% strength soln | Temp. | Time | Content of 3,5-difluoroaniline | Content of 3,5-difluorochloro-benzene (starting material) |
| 1 | 0.05 mol | 0.015 mol of CuCl | 0.015 mol of Cu powder | 0.50 mol | 150° C. | 24 h | 78% of theory | 9% of theory |
| 2 | 0.05 mol | 0.015 mol of CuCl | 0.015 mol of Cu powder | 0.50 mol | 200° C. | 12 h | 74% of theory | 1% of theory |
| 3 | 0.05 mol | 0.010 mol of CuCl | 0.010 mol of Cu powder | 0.75 mol | 175° C. | 18 h | 76% of theory | 2% of theory |
| 4 | 0.05 mol | 0.010 mol of CuI | 0.010 mol of Cu powder | 0.75 mol | 180° C. | 24 h | 76% of theory | 1% of theory |
| A | 0.05 mol | 0.010 mol of CuI | — | 0.75 mol | 175° C. | 18 h | 50% of theory | 1% of theory** |
| B | 0.05 mol | — | 0.010 mol of Cu powder | 0.75 mol | 175° C. | 18 h | 21% of theory | 10% of theory*** |
| 5 | 0.05 mol | 0.005 mol of Cu$_2$O | 0.010 mol of Cu powder | 0.75 mol | 180° C. | 24 h | 45% of theory | 30% of theory |
| 6 | 0.05 mol | 0.010 mol of CuI | 1 g steel turnings | 0.75 mol | 180° C. | 24 h | 75% of theory | 4% of theory |

*gas-chromatographic analysis with an internal standard
**When using CuI without addition of metal unselective decomposition occurs to a great extent
***The main product in the reaction with copper powder only is 3-fluoro-5-chloro-aniline.

Comparison Example A

Preparation of 3,5-difluoroaniline by reaction of 3,5-difluorochlorobenzene in the presence of a copper compound, but without addition of a metal A 100 ml autoclave having a Teflon liner is charged with the amount of 3,5-difluorochlorobenzene, CuI as copper compound and aqueous ammonia solution (25% by weight ammonia) indicated in the following table and the reaction is carried out as described in Examples 1 to 6. The addition of a metal is dispensed with.

To a great extent, tarry products are formed. The conversion is almost quantitative; the content of 3,5-difluoroaniline is only 50% of theory.

Comparison Example B

Preparation of 3,5-difluoroaniline by reaction of 3,5-difluorochlorobenzene in the presence of copper as a metal, but without addition of a copper compound A 100 ml autoclave having a Teflon liner is charged with the amount of 3,5-difluorochlorobenzene, copper powder as a metal and aqueous ammonia solution (25% by weight ammonia) indicated in the following table and the reaction

We claim:
1. A process for the preparation of 3,5-difluoroaniline, which comprises:
reacting 3,5-difluorochlorobenzene with ammonia in the presence of a solvent and a catalyst at 100 to 250° C.;
said catalyst comprising a copper compound and at least one metal, said metal being selected from the group consisting of copper, iron, cobalt, nickel, chromium, molybdenum and zinc.
2. The process as claimed in claim 1, wherein ammonia and 3,5-difluorochlorobenzene are employed in the molar ratio (1 to 100):1.
3. The process as claimed in claim 1, wherein ammonia and 3,5-difluorochlorobenzene are employed in the molar ratio (5 to 30):1.
4. The process as claimed in claim 1, wherein ammonia and 3,5-difluorochlorobenzene are employed in the molar ratio (10 to 20):1.
5. The process as claimed in claim 1, wherein the solvent employed is water or a mixture containing water and a water-soluble solvent.
6. The process as claimed in claim 1, wherein the solvent employed is water.
7. The process as claimed in claim 1, wherein ammonia is employed in the form of a 10 to 35% by weight ammonia-containing aqueous solution.

8. The process as claimed in claim 1, wherein ammonia is employed in the form of a 15 to 30% by weight ammonia-containing aqueous solution.

9. The process as claimed in claim 1, wherein the copper compound employed is a copper(I) compound, a copper(II) compound or a mixture thereof.

10. The process as claimed in claim 1, wherein the copper compound employed is a copper(I) salt or copper(I) oxide.

11. The process as claimed in claim 1, wherein the copper compound employed is copper(I) chloride, copper(I) bromide or copper(I) iodide.

12. The process as claimed in claim 1, wherein the reaction is carried out in the presence of at least one metal selected from the group consisting of copper, iron, cobalt and nickel.

13. The process as claimed in claim 1, wherein the reaction is carried out in the presence of at least one metal selected from the group consisting of copper, iron and cobalt.

14. The process as claimed in claim 1, wherein the metal employed is copper or iron.

15. The process as claimed in claim 1, wherein the metal employed is copper.

16. The process as claimed in claim 1, wherein the copper compound and 3,5-difluorochlorobenzene are employed in the molar ratio (0.05 to 1.5):1.

17. The process as claimed in claim 1, wherein the copper compound and 3,5-difluorochlorobenzene are employed in the molar ratio (0.1 to 0.6):1, in particular (0.15 to 0.4):1.

18. The process as claimed in claim 1, wherein (0.05 to 1.5) g atom of metal are employed per mole of 3,5-difluorochlorobenzene.

19. The process as claimed in claim 1, wherein (0.1 to 0.6), in particular (0.15 to 0.4) g atom of metal are employed per mole of 3,5-difluorochlorobenzene.

20. The process as claimed in claim 1, wherein the reaction is carried out at 130 to 200° C.

21. The process as claimed claim 1, wherein the reaction is carried out at 140 to 190° C.

22. The process as claimed in claim 1, wherein a 3,5-difluorochlorobenzene prepared from 1,3,5-trichlorobenzene by fluorine-chlorine exchange is employed.

* * * * *